(12) United States Patent
Horton et al.

(10) Patent No.: US 8,552,225 B2
(45) Date of Patent: Oct. 8, 2013

(54) PROCESS FOR VAPORIZING ACETIC ACID FOR HYDROGENATION PROCESSES TO PRODUCE ETHANOL

(75) Inventors: Trinity Horton, Houston, TX (US); Radmila Jevtic, Houston, TX (US); Victor J. Johnston, Houston, TX (US); R. Jay Warner, Houston, TX (US); Heiko Weiner, Pasadena, TX (US); Al Amleh, Pearland, TX (US); Gerald Gruesendorf, Rosharon, TX (US)

(73) Assignee: Celanese International Corporation, Dallas, TX (US)

( * ) Notice: Subject to any disclaimer, the term of this patent is extended or adjusted under 35 U.S.C. 154(b) by 346 days.

(21) Appl. No.: 12/974,982

(22) Filed: Dec. 21, 2010

(65) Prior Publication Data
US 2011/0257442 A1   Oct. 20, 2011

Related U.S. Application Data

(60) Provisional application No. 61/300,815, filed on Feb. 2, 2010, provisional application No. 61/332,696, filed on May 7, 2010, provisional application No. 61/332,699, filed on May 7, 2010.

(51) Int. Cl.
*C07C 29/153* (2006.01)
*C07C 29/154* (2006.01)

(52) U.S. Cl.
USPC ........................................................ 568/885

(58) Field of Classification Search
USPC ........................................................ 568/885
See application file for complete search history.

(56) References Cited

U.S. PATENT DOCUMENTS

| | | |
|---|---|---|
| 2,649,407 A | 8/1953 | Harrison et al. |
| 2,702,783 A | 2/1955 | Harrison et al. |
| 2,744,939 A | 5/1956 | Kennel |
| 2,882,244 A | 4/1959 | Milton |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,395,576 A | 7/1983 | Kwantes et al. |
| 4,398,039 A | 8/1983 | Pesa et al. |
| 4,421,939 A | 12/1983 | Kiff et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis et al. |
| 4,492,808 A | 1/1985 | Hagen et al. |
| 4,497,967 A | 2/1985 | Wan |
| 4,517,391 A | 5/1985 | Schuster et al. |
| 4,541,897 A | 9/1985 | Sommer et al. |
| 4,626,321 A | 12/1986 | Grethlein et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,826,795 A | 5/1989 | Kitson et al. |
| 4,842,693 A | 6/1989 | Wheldon et al. |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg et al. |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,215,902 A | 6/1993 | Tedder |
| 5,233,099 A | 8/1993 | Tabata et al. |
| 5,237,108 A | 8/1993 | Marraccini et al. |
| 5,250,271 A | 10/1993 | Horizoe et al. |

(Continued)

FOREIGN PATENT DOCUMENTS

| | | |
|---|---|---|
| EP | 104197 | 4/1984 |
| EP | 0167300 | 1/1986 |

(Continued)

OTHER PUBLICATIONS

Acala, et al., (2005). Experimental and DFT studies of the conversion of ethanol and acetic acid on PtSn-based catalysts, Journal of Physical Chemistry, 109(6), 2074-2085.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Hilmen, Separation of Azeotropic Mixtures: Tools for Analysis and Studies on Batch Distillation Operation (Nov. 2000) pp. 17-20.

(Continued)

*Primary Examiner* — Sikarl Witherspoon

(57) ABSTRACT

Vaporizing acetic acid in the presence of hydrogen to provide a vapor feed stream for a hydrogenation process that produces ethanol. The vaporizer forms a vapor feed stream and a blowdown stream having a weight ratio of the vapor feed stream to the blowdown stream of at least 2:1. The acetic acid may vaporized at a temperature below acetic acid's boiling point at the operating pressure of the reactor. The hydrogenation process produces a crude ethanol product and ethanol is separated from the crude product. In addition, at least one recycle stream comprising acetic acid and less than 1.0 wt. % compounds having a boiling point higher than acetic acid, may also be separated. The recycle streams may be introduced to the vaporizer along with acetic acid to form the vapor feed stream.

26 Claims, 2 Drawing Sheets

(56) References Cited

U.S. PATENT DOCUMENTS

| | | |
|---|---|---|
| 5,254,758 A | 10/1993 | Hiles et al. |
| 5,449,440 A | 9/1995 | Rescalli et al. |
| 5,565,068 A | 10/1996 | Parker et al. |
| RE35,377 E | 11/1996 | Steinberg et al. |
| 5,599,976 A | 2/1997 | Scates et al. |
| 5,770,770 A | 6/1998 | Kim et al. |
| 5,821,111 A | 10/1998 | Gaddy et al. |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,375,807 B1 | 4/2002 | Nieuwouldt et al. |
| 6,509,180 B1 | 1/2003 | Verser et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,115,772 B2 | 10/2006 | Picard et al. |
| 7,208,624 B2 | 4/2007 | Scates et al. |
| 7,297,236 B1 | 11/2007 | Vander et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,732,173 B2 | 6/2010 | Mairal et al. |
| 2006/0019360 A1 | 1/2006 | Verser et al. |
| 2006/0127999 A1 | 6/2006 | Verser et al. |
| 2007/0270511 A1 | 11/2007 | Melnichuk et al. |
| 2008/0135396 A1 | 6/2008 | Blum |
| 2009/0014313 A1 | 1/2009 | Lee et al. |
| 2009/0023192 A1 | 1/2009 | Verser et al. |
| 2009/0081749 A1 | 3/2009 | Verser et al. |
| 2009/0166172 A1 | 7/2009 | Casey |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Weiner et al. |
| 2010/0197485 A1 | 8/2010 | Johnston et al. |

FOREIGN PATENT DOCUMENTS

| | | |
|---|---|---|
| EP | 0456647 | 11/1991 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| WO | WO 83/03409 | 10/1983 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2009/105860 | 9/2009 |
| WO | WO 2010/055285 | 5/2010 |

OTHER PUBLICATIONS

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.
International Search Report and Written Opinion for PCT/US2011/023332 mailed Sep. 9, 2011.
Written Opinion for PCT/US2011/023332 mailed May 8, 2012.
International Preliminary Report on Patentability for PCT/US2011/023332 mailed Jun. 25, 2012.

PROCESS FOR VAPORIZING ACETIC ACID FOR HYDROGENATION PROCESSES TO PRODUCE ETHANOL

CROSS REFERENCE TO RELATED APPLICATIONS

This application claims priority to U.S. Provisional App. No. 61/300,815, filed on Feb. 2, 2010, U.S. Provisional App. No. 61/332,696, filed on May 7, 2010, and U.S. Provisional App. No. 61/332,699, filed on May 7, 2010, the entire contents and disclosures of which are incorporated herein by reference.

FIELD OF THE INVENTION

The present invention relates generally to hydrogenation processes to produce ethanol, and, in particular, to processes for vaporizing acetic acid that is hydrogenated.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol for fuels or consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. Hydrogenation of alkanoic acids and/or other carbonyl group-containing compounds may be carried out in the liquid phase, as described in U.S. Pat. No. 4,480,115. In the liquid phase, acetic acid is extremely corrosive and may destroy the catalysts and/or reaction equipment. U.S. Pat. No. 4,517,391 describes a cobalt catalyst for hydrogenating acetic acid in the vapor phase by feeding liquid acetic acid to the reactor. The acetic acid is vaporized in the reactor under the reaction conditions. U.S. Pat. No. 4,777,303 also reacts acetic acid in the vapor phase.

During the reduction of alkanoic acid, e.g., acetic acid, other compounds are formed with ethanol or are formed in side reactions. These byproducts and/or impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol. The impurities may also build up in the recovery system.

Therefore, a need remains for improving vaporization of acetic acid for hydrogenation of acetic acid.

SUMMARY OF THE INVENTION

In a first embodiment, the present invention is directed to a process for producing ethanol, comprising introducing acetic acid into a vaporizer to form a vapor feed stream and a blowdown stream having a weight ratio of the vapor feed stream to the blowdown stream of at least 2:1. The vapor feed stream is introduced to a reactor and acetic acid is hydrogenated from the vapor feed stream in the presence of a catalyst to form a crude ethanol product comprising ethanol.

In a second embodiment, the present invention is directed to a process for producing ethanol, comprising the steps of introducing acetic acid in a vaporizer to form a vapor feed stream, introducing the vapor feed stream into a reactor, and hydrogenating acetic acid from the vapor feed stream in the presence of a catalyst to form a crude ethanol product comprising ethanol. The process further comprises separating ethanol and at least one recycle stream from the crude ethanol product. The recycle stream comprises acetic acid and less than 1.0 wt. % compounds having a boiling point higher than acetic acid. In addition, the recycle stream is introduced to the vaporizer along with acetic acid to form the vapor feed stream.

In a third embodiment, the present invention is directed to a process for producing ethanol, comprising the steps of vaporizing acetic acid in a vaporizer in the presence of hydrogen to form a vapor feed stream comprising vaporized acetic acid, introducing the vapor feed stream into a reactor, and hydrogenating the vaporized acetic acid at an operating pressure of the reactor and in the presence of a catalyst to form a crude ethanol product comprising ethanol. Preferably, the acetic acid is vaporized at a temperature below acetic acid's boiling point at an operating pressure of the reactor. The operating pressure of the reactor may be from 10 KPa to 3000 KPa.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
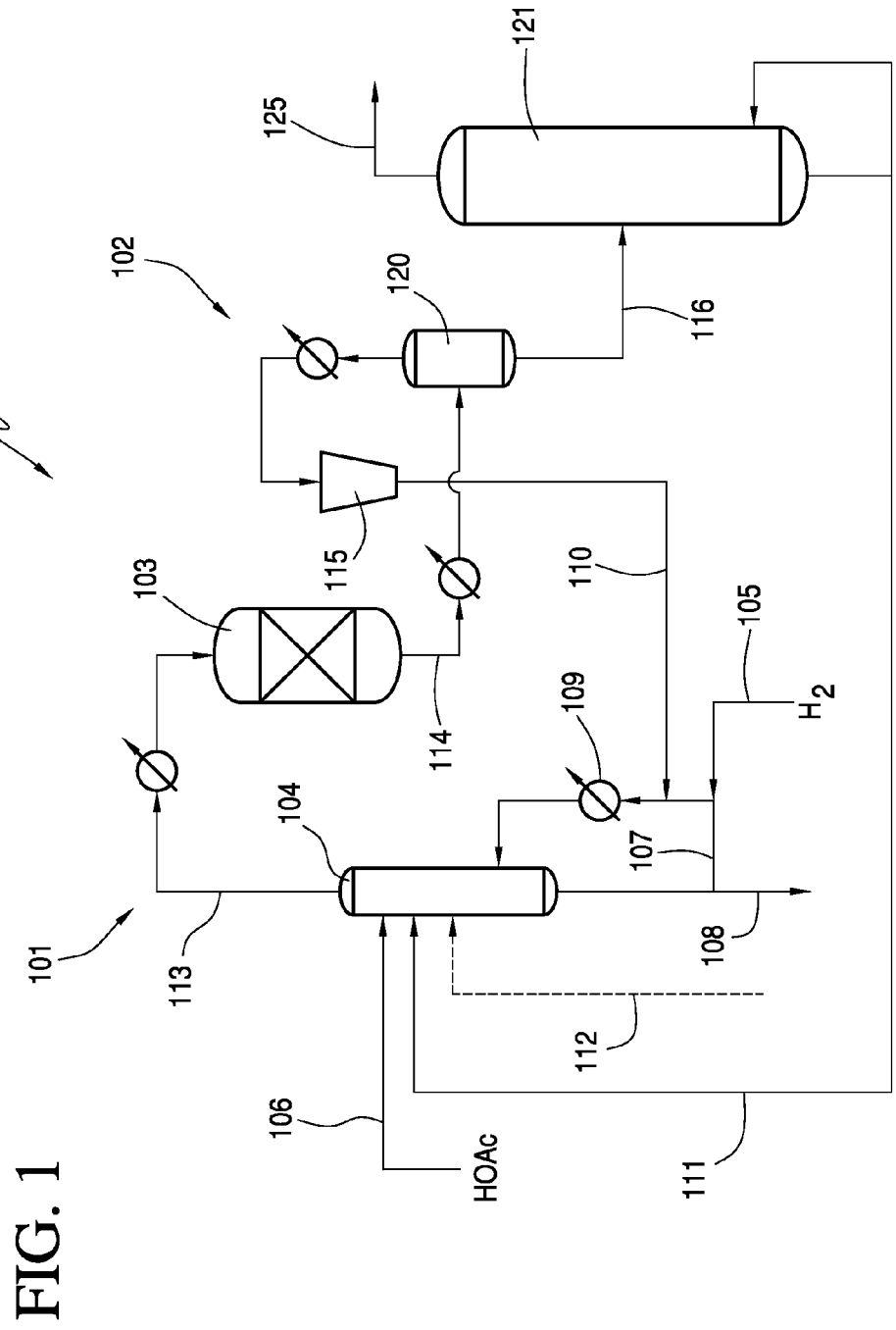
FIG. 1 is a schematic diagram of a hydrogenation system in accordance with one embodiment of the present invention.

The present invention relates to processes for vaporizing acetic acid to be fed to a hydrogenation process. The vaporized acetic acid is hydrogenated in the presence of a catalyst to form a crude reactor product that comprises ethanol. Embodiments of the present invention recover ethanol from the crude reactor product. The hydrogenation process is preferably conducted in the vapor phase. In one embodiment, acetic acid may be vaporized prior to the hydrogenation. Acetic acid in the vapor phase is less corrosive than acetic acid in the liquid phase. However, acetic acid in the vapor phase may be corrosive near its dew point. Embodiments of the present invention avoid these corrosive environments by vaporizing acetic acid below its boiling point in the reaction.

After acetic acid is hydrogenated, a purification system separates the crude reactor product into several streams containing byproducts and impurities. These byproducts and impurities may be recycled to the reactor. Preferably, the recycle streams are vaporized along with the acetic acid. This may lead to a build up in heavier byproducts and impurities in the vaporizer that require a blowdown stream to purge the heavier components. Depending on the quality, the fresh acetic acid feed may also contain heavier components. Generally purges must be discarded and have little economical benefit and thus represent an inefficient and additional costs for handling. The recycle streams of the present invention may contain small amounts of heavier components. It is also believed that few side reactions occur in the vaporizer that form heavier components. In embodiments of the present invention, the vaporization of acetic acid may have a small blowdown stream, even when recycle streams are fed to the vaporizer. In one embodiment, the blowdown stream may need to be purged intermittently. A small blowdown stream or one that needs intermittent purging may allow a significant portion of the feed to be vaporized and directed to the reactor. In addition, the blowdown stream may have a high concentration of acetic acid and it may be reused. Advantageously, the small blowdown stream provides for improved efficiencies.

In embodiments of the present invention, the acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment the acetic acid may be vaporized at the boiling point of acetic acid at the operating pressure of the hydrogenation reactor, and then the vaporized acetic acid may be further heated to the reactor inlet temperature. The acetic acid may be transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor by passing hydrogen and/or recycle gas through the acetic acid at a temperature at or below 125° C., followed by heating of the combined gaseous stream to the reactor inlet temperature.

Figure 2:
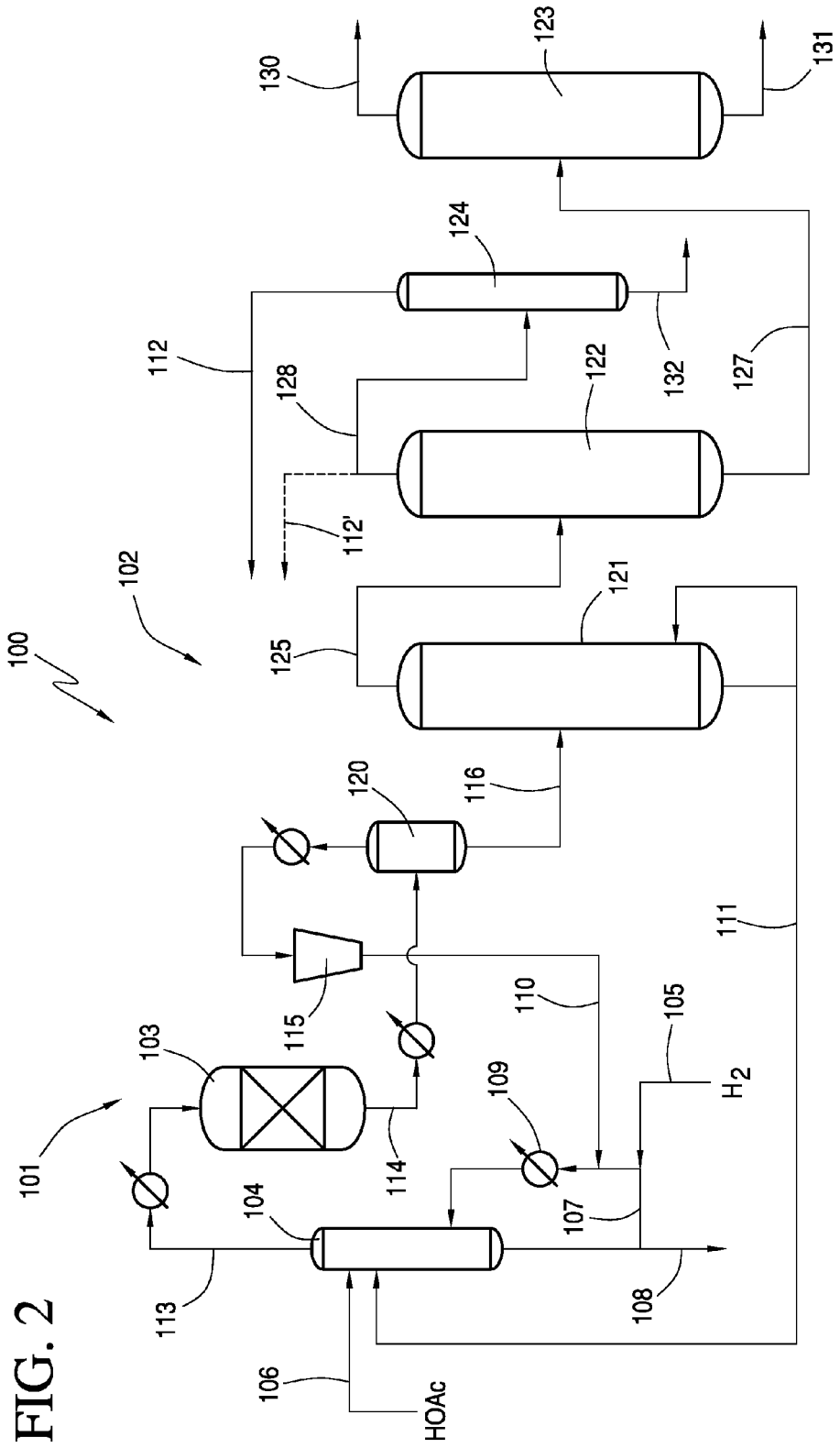
FIG. 2 is a schematic diagram of the reaction zone in accordance with one embodiment of the present invention.

FIGS. 1 and 2 show a hydrogenation system 100 suitable for the hydrogenation of acetic acid and separating ethanol from the crude reaction mixture according to one embodiment of the invention. System 100 comprises reaction zone 101 and purification zone 102. Reaction zone 101 comprises reactor 103, vaporizer 104, hydrogen feed line 105, and acetic acid feed line 106. In FIG. 1, purification zone 102 comprises flasher 120 and first column 121. In FIG. 2, purification zone 102 further comprises second column 122, third column 123, and fourth column 124.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, such a process can also be used to make hydrogen which may be used in connection with this invention.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the disclosure of which is incorporated herein by reference. Optionally, the production of ethanol may be integrated with such methanol carbonylation processes.

U.S. Pat. No. RE 35,377 also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syn gas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas as well as U.S. Pat. No. 6,685,754, the disclosures of which are incorporated herein by reference.

In one optional embodiment, the acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the present of carboxylic acids, such as propanoic acid or its anhydride, may be beneficial in producing propanol.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

Hydrogen feed line 105 may be fed to reboiler stream 107 that provides heat input to vaporizer 104. This allows hydrogen feed line 105 to be fed to a lower portion of vaporizer 104. Reboiler stream 107 also comprises a portion of residue that is circulated through reboiler 109 along with hydrogen feed line 105. In some embodiment, the residue may comprise a portion of blowdown stream 108. Hydrogen feed line 105 may be preheated to a temperature from 30° C. to 150° C., e.g., from 50° C. to 125° C. or from 60° C. to 115° C. Hydrogen feed line 105 may be fed at a pressure from 1300 KPa to 3100 KPa, e.g., from 1500 KPa to 2800 KPa, or 1700 KPa to 2600 KPa. Optionally, hydrogen feed line 105 may be fed to one or more separators, such as guard beds, pressure-swing absorbers, membranes, or combinations thereof, to remove impurities, such as carbon monoxide and carbon dioxide, in hydrogen feed line 105.

Reboiler stream 107 may further comprise unreacted hydrogen from recycle vapor stream 110. Recycle vapor stream 110 is obtained from flasher 120 as described below. Preferably, the pressure and temperature of recycle vapor stream 110 is similar to the fed temperature and pressure of hydrogen feed line 105. Recycle vapor stream 110 may be fed directly to reboiler stream 107 or mixed with hydrogen feed stream 105 and co-fed to reboiler stream 107.

Acetic acid feed line 106 may be fed to the upper portion of vaporizer 104. Preferably acetic acid feed line 106 is fed to vaporizer 104 in the liquid phase. Acetic acid feed line 106 may be preheated to a temperature from 30° C. to 150° C., e.g., from 50° C. to 125° C. or from 60° C. to 115° C. As indicated above, acetic acid feed line 106 may comprise acetic acid, acetic anhydride, acetaldehyde, ethyl acetate, and mixtures thereof. Optionally, acetic acid feed line 106 may be fed to one or more guard beds to remove impurities in the acetic acid feed line 106, such as halogens.

In addition to acetic acid feed line 106, a recycle stream 111 that comprises a portion of the residue from first column 121 may be fed to vaporizer 104. The residue of first column 121 comprises acetic acid and water. Preferably recycle stream 111 comprises less than 1.0 wt. % compounds having a boiling point higher than acetic acid, e.g., less than 0.5 wt. %, less than 0.25 wt. % or less than 0.15 wt. %. Compounds having a boiling point higher than acetic acid may include heavy compounds such as acetic anhydride, and propanoic acid.

Optionally, one or more further recycle streams 112 may also be fed to vaporizer 104. Preferably when these one or more further recycle streams 112 and recycle stream 111 together comprises less than 1.0 wt. % compounds having a boiling point higher than acetic acid, e.g., less than 0.5 wt. % or less than 0.25 wt. %. These optional recycle stream 112 may be obtained from purification zone 102 and may comprise unreacted acetic acid, acetaldehyde, ethyl acetate, water, ethanol and mixtures thereof. In one embodiment, recycle stream 111 or optional recycle stream 112 may be combined and mixed with acetic acid feed line 106 prior to be fed to vaporizer 104.

Vaporizer 104 produces a vapor feed stream 113 by transferring the acetic acid from the liquid to gas phase below the boiling point of acetic acid in reactor 103 at the operating pressure of the reactor. In one embodiment, the acetic acid in the liquid state is maintained at a temperature of below 160° C., e.g., below 150° C. or below 130° C. The vaporizer may be operated at a temperature of at least 118° C. Acetic acid can be corrosive at its dew point, and keeping the acetic acid below its boiling point in the reactor may reduce the corrosive tendency of acetic acid. Advantageously, vaporizer 104 used for embodiments of the present invention may be constructed of stainless steel and similar materials including, but not limited to, SS316, SS316L, SS317, 2205, HASTELLOY™ B (Haynes International), HASTELLOY™ C. Embodiments of the present invention may eliminate or reduce the need for higher grade materials, thus reducing costs.

The temperature of vapor feed stream 113 is preferably from 100° C. to 350° C., e.g., from 120° C. to 310° C. or from 150° C. to 300° C. Vapor feed stream 113 may be pre-heated and fed to reactor 103. Preferably in one embodiment, the temperature of vapor feed stream 113 may be about 120° C. upon exiting the vaporizer 104 and preheated to a temperature of about 200° C. to 250° C. before being fed to reactor 103. Vapor feed stream 113 may be preheated by indirect-contact heat exchangers with another stream such as the reactor effluent.

In one embodiment, the weight ratio of vapor feed stream 113 to blowdown stream 108 is at least 2:1, e.g., at least 5:1 or at least 10:1. Advantageously, embodiments of the present invention may allow for a relatively small blowdown stream 108, and the weight ratio may be from 2:1 to 250:1, e.g., 5:1 to 200:1 or 10:1 to 175:1. Preferred weight ratios are at least 17:1, e.g., at least 70:1 or at least 160:1.

Preferably, vapor feed stream 113 comprises at least 70 wt. % acetic acid based on the total weight of the vapor feed stream, e.g., at least 80 wt. % or at least 90 wt. %. Blowdown stream 108 preferably comprises at least 85 wt. % acetic acid, e.g., at least 90 wt. % or at least 95 wt. %. Preferably when blowdown stream 108 comprises less than 1.0 wt. % compounds having a boiling point higher than acetic acid, e.g., less than 0.5 wt. % or less than 0.25 wt. %. In optional embodiment there may be a sample valve to monitor blowdown stream 108 for analysis of the composition. Vapor feed stream 113 and blowdown stream 108 may also comprise hydrogen, acetaldehyde, ethanol, methyl acetate, ethyl acetate, water, acetone, methyl acetate, and mixtures thereof. Additional components of blowdown stream 108 may include ethylidene diacetate, 1,3-butylene glycol diacetate, and/or n-butyl benzoate. In one embodiment, as the weight ratio increases, the acetic acid purity of blowdown stream 108 may also increase. This allows blowdown stream 108 to be used in the hydrogenation process or used in other chemical processes, rather than being discarded.

FIG. 1 shows vapor feed stream 113 being directed to the top of reactor 103, and in some other embodiment vapor feed stream 113 may be directed to the side, upper portion, or bottom of reactor 103.

Reactor 103 contains the catalyst that is used in the hydrogenation of the carboxylic acid, preferably acetic acid. Suitable hydrogenation catalysts include catalysts comprising a first metal and optionally one or more of a second metal, a third metal or additional metals, optionally on a catalyst support. The first and optional second and third metals may be selected from Group IB, IIB, IIIB, IVB, VB, VIIB, VIIB, VIII transitional metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. No. 7,608,744 and U.S. Pub. Nos. 2010/0029995 and 2010/0197485, the entireties of which are incorporated herein by reference.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal preferably is present in an amount from 0.1 and 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 and 4 wt. %, e.g., from 0.1 to 3 wt. %, or from 0.1 to 2 wt. %.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

In the production of ethanol, the catalyst support may be modified with a support modifier. Preferably, the support modifier is a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. Preferably, the support modifier is a calcium silicate, and more preferably calcium metasilicate ($CaSiO_3$). If the support modifier comprises calcium metasilicate, it is preferred that at least a portion of the calcium metasilicate is in crystalline form.

A preferred silica support material is SS61138 High Surface Area (HSA) Silica Catalyst Carrier from Saint-Gobain NorPro. The Saint-Gobain NorPro SS61138 silica contains approximately 95 wt. % high surface area silica; a surface area of about 250 $m^2$/g; a median pore diameter of about 12 nm; an average pore volume of about 1.0 $cm^3$/g as measured by mercury intrusion porosimetry and a packing density of about 0.352 $g/cm^3$ (22 $lb/ft^3$).

A preferred silica/alumina support material is KA-160 (Sud Chemie) silica spheres having a nominal diameter of about 5 mm, a density of about 0.562 g/ml, in absorptivity of about 0.583 g $H_2O$/g support, a surface area of about 160 to 175 $m^2$/g, and a pore volume of about 0.68 ml/g.

As will be appreciated by those of ordinary skill in the art, support materials are selected such that the catalyst system is suitably active, selective and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744 and U.S. Pub. Nos. 2010/0029995 and 2010/0197485, referred to above, the entireties of which are incorporated herein by reference.

Suitable reactors may include a variety of configurations using a fixed bed reactor or a fluidized bed reactor, as one of skill in the art will readily appreciate. In many embodiments of the present invention, an "adiabatic" reactor can be used; that is, there is little or no need for internal plumbing through the reaction zone to add or remove heat. In other embodiments, radial flow reactor or reactors may be employed, or a series of reactors may be employed with or with out heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction preferably is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not detectable. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour is preferred, e.g., at least 400 or at least 600. In terms of ranges, the productivity preferably is from 200 to 3,000 grams of ethanol per kilogram catalyst per hour, e.g., from 400 to 2,500 or 600 to 2,000.

In various embodiments, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. In some exemplary embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably from 0 to 90 wt. %, e.g., from 5 to 80 wt. %, from 15 to 70 wt. %, from 20 to 70 wt. % or from 25 to 65 wt. %. As water is formed in the reaction process, water will generally be present in the crude ethanol product, for example, in amounts ranging from 5 to 35 wt. %, e.g., from 10 to 30 wt. % or from 10 to 26 wt. %. Ethyl acetate may also be produced during the hydrogenation of acetic acid or through side reactions and may be present, for example, in amounts ranging from 0 to 20 wt. %, e.g., from 0 to 15 wt. %, from 1 to 12 wt. % or from 3 to 10 wt. %. Acetaldehyde may also be produced through side reactions and may be present, for example, in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, ketones, alkanes, and carbon dioxide, if detectable, collectively may be present in amounts less than 10 wt. %, e.g., less than 6 wt. % or less than 4 wt. %. In terms of ranges, other components may be present in an amount from 0.1 to 10 wt. %, e.g., from 0.1 to 6 wt. %, or from 0.1 to 4 wt. %. Exemplary embodiments of crude ethanol compositional ranges are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

During the hydrogenation process, a crude ethanol product is withdrawn, preferably continuously, from reactor 103 via line 114. The crude ethanol product may be condensed and fed to flasher 120, which, in turn, provides a vapor stream and a liquid stream. Flasher 120 preferably operates at a temperature from 50° C. to 500° C., e.g., from 70° C. to 400° C. or from 100° C. to 350° C. In one embodiment, the pressure of flasher 120 preferably is from 50 KPa to 2000 KPa, e.g., from 75 KPa to 1500 KPa or from 100 to 1000 KPa. In one embodiment the temperature and pressure of flasher 120 may be similar to the temperature and/or pressure of reactor 103.

The vapor stream exiting flasher 120 may comprise hydrogen and hydrocarbons, which may be purged and/or returned to reaction zone 101 via line 110. As shown in FIG. 1, the returned portion of the vapor stream passes through compressor 115 and is combined with reboiler stream 107.

The liquid from flasher 120 is withdrawn and pumped as a feed composition via line 116 to the side of first column 121, also referred to as the acid separation column. The contents of line 116 typically will be substantially similar to the product obtained directly from the reactor, and may, in fact, also be characterized as a crude ethanol product. However, the feed composition in line 116 preferably has substantially no hydrogen, carbon dioxide, methane or ethane, which are removed by flasher 120. Exemplary components of liquid in line 116 are provided in Table 2. It should be understood that liquid line 116 may contain other components, not listed, such as components in the feed.

TABLE 2

FEED COMPOSITION

|  | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 116, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

When the content of acetic acid in line 116 is less than 5 wt. %, the acid separation column 121 may be skipped and line 116 may be introduced directly to second column 122, also referred to herein as a light ends column.

In the embodiment shown in FIG. 1, line 116 is introduced in the lower part of first column 121, e.g., lower half or lower third. In first column 121, unreacted acetic acid, a portion of the water, and other heavy components, if present, are removed from the composition in line 116 and are withdrawn, preferably continuously, as residue. Some or all of the residue may be returned and/or recycled back to reaction zone 101 via line 111. First column 121 also forms an overhead distillate, which is withdrawn in line 125, and which may be condensed and refluxed, for example, at a ratio from 10:1 to 1:10, e.g., from 3:1 to 1:3 or from 1:2 to 2:1.

Any of columns 121, 122, 123, or 124 may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIGS. 1 and 2. As shown in FIGS. 1 and 2, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and one flasher are shown in FIGS. 1 and 2, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 KPa to 3000 KPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependent on the composition of the material at that location and the pressure of column. In addition, feed rates may vary depending on the size of the production process and, if described, may be generically referred to in terms of feed weight ratios.

When column 121 is operated under standard atmospheric pressure, the temperature of the residue exiting in line 111 from column 121 preferably is from 95° C. to 120° C., e.g., from 105° C. to 117° C. or from 110° C. to 115° C. The temperature of the distillate exiting in line 125 from column 121 preferably is from 70° C. to 110° C., e.g., from 75° C. to 95° C. or from 80° C. to 90° C. In other embodiments, the pressure of first column 121 may range from 0.1 KPa to 510 KPa, e.g., from 1 KPa to 475 KPa or from 1 KPa to 375 KPa. Exemplary components of the distillate and residue compositions for first column 121 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN

| | Conc. (wt. %) | Conc. (wt. %) | Conc. (wt. %) |
|---|---|---|---|
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column 121 (first column), the acetal appears to decompose in the column such that less or even no detectable amounts are present in the distillate and/or residue.

Depending on the reaction conditions, the crude ethanol product exiting reactor 103 in line 114 may comprise ethanol, acetic acid (unconverted), ethyl acetate, and water. After exiting reactor 103, a non-catalyzed equilibrium reaction may occur between the components contained in the crude ethanol product until it is added to flasher 120 and/or first column 121. This equilibrium reaction tends to drive the crude ethanol product to an equilibrium between ethanol/acetic acid and ethyl acetate/water, as shown below.

$$EtOH + HOAc \leftrightarrows EtOAc + H_2O$$

In the event the crude ethanol product is temporarily stored, e.g., in a holding tank, prior to being directed to purification zone 102, extended residence times may be encountered. Generally, the longer the residence time between reaction zone 101 and purification zone 102, the greater the formation of ethyl acetate. For example, when the residence time between reaction zone 101 and purification zone 102 is greater than 5 days, significantly more ethyl acetate may form at the expense of ethanol. Thus, shorter residence times between reaction zone 101 and purification zone 102 are generally preferred in order to maximize the amount of ethanol formed. In one embodiment, a holding tank (not shown), is included between the reaction zone 101 and purification zone 102 for temporarily storing the liquid component from line 116 for up to 5 days, e.g., up to 1 day, or up to 1 hour. In a preferred embodiment no tank is included and the condensed liquids are fed directly to the first distillation column 121. In addition, the rate at which the non-catalyzed reaction occurs may increase as the temperature of the crude ethanol product, e.g., in line 116, increases. These reaction rates may be particularly problematic at temperatures exceeding 30° C., e.g., exceeding 40° C. or exceeding 50° C. Thus, in one embodiment, the temperature of liquid components in line 116 or in the optional holding tank is maintained at a temperature less than 40° C., e.g., less than 30° C. or less than 20° C. One or more cooling devices may be used to reduce the temperature of the liquid in line 116.

As discussed above, a holding tank (not shown) may be included between the reaction zone 101 and purification zone 102 for temporarily storing the liquid component from line 116, for example from 1 to 24 hours, optionally at a temperature of about 21° C., and corresponding to an ethyl acetate formation from 0.01 wt. % to 1.0 wt. % to 1.0 wt % respectively. In addition, the rate at which the non-catalyzed reaction occurs may increase as the temperature of the crude ethanol product is increased. For example, as the temperature of the crude ethanol product in line 116 increases from 4° C. to 21° C., the rate of ethyl acetate formation may increase from about 0.01 wt. % per hour to about 0.005 wt. % per hour. Thus, in one embodiment, the temperature of liquid components in line 116 or in the optional holding tank is maintained at a temperature less than 21° C., e.g., less than 4° C. or less than −10° C.

In addition, it has now been discovered that the above-described equilibrium reaction may also favor ethanol formation in the top region of first column 121.

The distillate, e.g., overhead stream, of column 121 optionally is condensed and refluxed, preferably, at a reflux ratio of 1:5 to 10:1. The distillate in line 125 preferably comprises ethanol, ethyl acetate, and water, along with other impurities, which may be difficult to separate due to the formation of binary and tertiary azeotropes.

The first distillate in line 125 is introduced to the second column 122, also referred to as the "light ends column," preferably in the middle part of column 122, e.g., middle half or middle third. As one example, when a 25 tray column is utilized in a column without water extraction, line 125 is introduced at tray 17. In one embodiment, the second column 122 may be an extractive distillation column. In such embodiments, an extraction agent, such as water, may be added to second column 122. If the extraction agent comprises water, it may be obtained from an external source or from an internal return/recycle line from one or more of the other columns, such as from the residue of third column 123 from line 131.

Second column 122 may be a tray column or packed column. In one embodiment, second column 122 is a tray column having from 5 to 70 trays, e.g., from 15 to 50 trays or from 20 to 45 trays.

Although the temperature and pressure of second column 122 may vary, when at atmospheric pressure the temperature of the second residue exiting in line 127 from second column 122 preferably is from 60° C. to 90° C., e.g., from 70° C. to 90° C. or from 80° C. to 90° C. The temperature of the second distillate exiting in line 128 from second column 122 preferably is from 50° C. to 90° C., e.g., from 60° C. to 80° C. or from 60° C. to 70° C. Column 122 may operate at atmospheric pressure. In other embodiments, the pressure of second column 122 may range from 0.1 KPa to 510 KPa, e.g., from 1 KPa to 475 KPa or from 1 KPa to 375 KPa. Exemplary components for the distillate and residue compositions for second column 122 are provided in Table 4 below. It should be understood that the distillate and residue may also contain other components, not listed, such as components in the feed.

TABLE 4

SECOND COLUMN

| | Conc. (wt. %) | Conc. (wt. %) | Conc. (wt. %) |
|---|---|---|---|
| Distillate | | | |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue | | | |
| Water | 30 to 70 | 30 to 60 | 30 to 50 |
| Ethanol | 20 to 75 | 30 to 70 | 40 to 70 |

TABLE 4-continued

SECOND COLUMN

|  | Conc. (wt. %) | Conc. (wt. %) | Conc. (wt. %) |
|---|---|---|---|
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent in second column 122, the weight ratio of ethyl acetate in the second residue to ethyl acetate in the second distillate approaches zero.

As shown, the second residue from the bottom of second column 122, which comprises ethanol and water, is fed via line 127 to third column 123, also referred to as the "product column." More preferably, second residue in line 127 is introduced in the lower part of third column 123, e.g., lower half or lower third. Third column 123 recovers ethanol, which preferably is substantially pure other than the azeotropic water content, as the distillate in line 130. The distillate of third column 123 preferably is refluxed as shown in FIG. 1, for example, at a reflux ratio from 1:10 to 10:1, e.g., from 1:3 to 3:1 or from 1:2 to 2:1. The third residue in line 131, which preferably comprises primarily water, preferably is removed from system 100 or may be partially returned to any portion of system 100. In one embodiment, a portion of line 131 may be fed to second column 122 as the extractive agent. Third column 123 is preferably a tray column as described above and preferably operates at atmospheric pressure. The temperature of the third distillate exiting in line 130 from third column 123 preferably is from 60° C. to 110° C., e.g., from 70° C. to 100° C. or from 75° C. to 95° C. The temperature of the third residue 131 exiting from third column 123 preferably is from 70° C. to 115° C., e.g., from 80° C. to 110° C. or from 85° C. to 105° C., when the column is operated at atmospheric pressure. Exemplary components of the distillate and residue compositions for third column 123 are provided in Table 5 below. It should be understood that the distillate and residue may also contain other components, not listed, such as components in the feed.

TABLE 5

THIRD COLUMN

|  | Conc. (wt. %) | Conc. (wt. %) | Conc. (wt. %) |
|---|---|---|---|
| Distillate | | | |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue | | | |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 121, 122, 123, and/or 124 in system 100. Preferably at least one side stream is used to remove impurities from the third column 123. The impurities may be purged and/or retained within system 100.

The third distillate in line 130 may be further purified to form an anhydrous ethanol product stream, i.e., "finished anhydrous ethanol," using one or more additional separation systems, such as, for example, distillation columns (e.g., a finishing column) or molecular sieves.

Returning to second column 122, the second distillate 128 preferably is refluxed at a reflux ratio from 1:10 to 10:1, e.g., from 1:5 to 5:1 or from 1:3 to 3:1. A portion of second distillate 128 may be returned to reaction zone 101 via line 112'. Optionally, if returned to reaction zone, the portion of second distillate in line 112' may be fed to vaporizer 104. A portion of the second distillate may also be fed via line 128 to fourth column 124, also referred to as the "acetaldehyde removal column." In fourth column 124 the second distillate is separated into a fourth distillate, which comprises acetaldehyde, in line 112 and a fourth residue, which comprises ethyl acetate, in line 132. The fourth distillate preferably is refluxed at a reflux ratio from 1:20 to 20:1, e.g., from 1:15 to 15:1 or from 1:10 to 10:1, and a portion of the fourth distillate is returned to the reaction zone 101 as shown by line 112. For example, the fourth distillate may be combined with acetic acid feed 106, added to vaporizer 104, and/or added directly to reactor 103. Preferably, fourth distillate in line 112 is fed to vaporizer 104. Without being bound by theory, since acetaldehyde may be hydrogenated to form ethanol, the recycling of a stream that contains acetaldehyde to the reaction zone increases the yield of ethanol and decreases byproduct and waste generation. In another embodiment (not shown in the figure), the acetaldehyde may be collected and utilized, with or without further purification, to make useful products including but not limited to n-butanol, 1,3-butanediol, and/or crotonaldehyde and derivatives.

The fourth residue of fourth column 124 may be purged via line 132. The fourth residue primarily comprises ethyl acetate and ethanol, which may be suitable for use as a solvent mixture or in the production of esters. In one preferred embodiment, the acetaldehyde is removed from the second distillate in fourth column 124 such that no detectable amount of acetaldehyde is present in the residue of column 124.

Fourth column 124 is preferably a tray column as described above and preferably operates above atmospheric pressure. In one embodiment, the pressure is from 120 KPa to 5,000 KPa, e.g., from 200 KPa to 4,500 KPa, or from 400 KPa to 3,000 KPa. In a preferred embodiment the fourth column 124 may operate at a pressure that is higher than the pressure of the other columns.

The temperature of the fourth distillate exiting in line 112 from fourth column 124 preferably is from 60° C. to 110° C., e.g., from 70° C. to 100° C. or from 75° C. to 95° C. The temperature of the residue exiting from fourth column 124 preferably is from 70° C. to 115° C., e.g., from 80° C. to 110° C. or from 85° C. to 110° C. Exemplary components of the distillate and residue compositions for fourth column 124 are provided in Table 6 below. It should be understood that the distillate and residue may also contain other components, not listed, such as components in the feed.

TABLE 6

FOURTH COLUMN

| | Conc. (wt. %) | Conc. (wt. %) | Conc. (wt. %) |
|---|---|---|---|
| Distillate | | | |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue | | | |
| Ethyl Acetate | 40 to 100 | 50 to 100 | 60 to 100 |
| Ethanol | <40 | 0.001 to 30 | 0 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

The finished ethanol composition obtained by the processes of the present invention preferably comprises from 75 to 96 wt. % ethanol, e.g., from 80 to 96 wt. % or from 85 to 96 wt. % ethanol, based on the total weight of the finished ethanol composition. Exemplary finished ethanol compositional ranges are provided below in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol is from 80 to 1,000 wppm, e.g., from 95 to 1,000 wppm, from 100 to 700 wppm, or from 150 to 500 wppm. In one embodiment, the finished ethanol composition preferably is substantially free of acetaldehyde and may comprise less than 8 wppm of acetaldehyde, e.g., less than 5 wppm or less than 1 wppm.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircrafts. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid or reacted with polyvinyl acetate. The finished ethanol composition may be dehydrated to produce ethylene. Any of known dehydration catalysts can be employed in to dehydrate ethanol, such as those described in U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

In order that the invention disclosed herein may be more efficiently understood, an example is provided below. The following examples describe the processes of the present invention.

Examples

A fresh feed stream of acetic acid and a recycle stream was fed to a vaporizer. The recycle stream from the purification zone comprised acetic acid (~83 wt. %), water (~10 wt. %), ethyl acetate (~3.5 wt. %), ethanol (~2 wt. %), acetaldehyde (~1.5 wt. %) and other trace impurities such as methyl acetate and acetone. The vaporizer was carried out at a pot temperature of 107-117° C. and a vapor temperature of about 100° C. Table 8 summarizes the distillate and residue composition at different weight ratios of the vapor to blowdown streams.

TABLE 8

| | Vapor to Blowdown Weight Ratio | | | |
|---|---|---|---|---|
| | 2:1 | 17:1 | 70:1 | 160:1 |
| Distillate (Vapor) | | | | |
| Acetaldehyde | 0.005 | 0.316 | 0.528 | — |
| Acetic Acid | 94.7 | 87.1 | 82.8 | 92.0 |
| Ethanol | 0.20 | 0.14 | 0.19 | 0.23 |
| Ethyl Acetate | 0.22 | 0.86 | 2.01 | — |
| $H_2O$ | 7.2 | 14.0 | 15.4 | 7.2 |
| Methyl Acetate | — | 0.001 | — | 0.0014 |
| Residue (Blowdown) | | | | |
| Acetaldehyde | 0.358 | 0.004 | 0.039 | — |
| Acetic Acid | 86.9 | 97.6 | 99.7 | 98.7 |
| Ethanol | 0.512 | 0.017 | 0.018 | 0.006 |
| Ethyl Acetate | 2.05 | 0.04 | 0.17 | 0.02 |
| $H_2O$ | 12.5 | 2.4 | — | 0.0624 |

The residue samples collected ranged from a slightly light yellow color for the 2:1 ratio, to amber for the 17:1 ratio, and a dark green for the 160:1 ratio. A non-volatile analysis was conducted on the 70:1 ratio and found to have 0.368 wt. % residual solids. The non-volatile analysis was performed by heating the residue slowly in a platinum crucible in a heated sand bath at 130° C. for 3 hours.

Additional analysis of the residue samples from the 17:1 and 70:1 showed trace amounts of ethylidene diacetate, 1,3-butylene glycol diacetate, and n-butyl benzoate.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
   introducing acetic acid into a vaporizer to form a vapor feed stream and a blowdown stream having a weight ratio of the vapor feed stream to the blowdown stream of at least 2:1, and wherein the blowdown stream comprises at least 85 wt. % acetic acid;
   introducing the vapor feed stream into a reactor; and
   hydrogenating acetic acid from the vapor feed stream in the presence of a catalyst to form a crude ethanol product comprising ethanol.

2. The process of claim 1, wherein the reactor is operated at an operating pressure from 10 KPa to 3000 KPa, and the acetic acid is vaporized at a temperature below the acetic acid's boiling point at the operating pressure.

3. The process of claim 1, wherein the vapor feed stream temperature is less than 160° C.

4. The process of claim 1, wherein acetic acid is fed to an upper portion of the vaporizer.

5. The process of claim 1, wherein hydrogen is fed to a lower portion of the vaporizer.

6. The process of claim 1, wherein the weight ratio of the vapor feed stream to the blowdown stream is at least 10:1.

7. The process of claim 6, wherein the blowdown stream comprises less than 1 wt. % of compounds having a boiling point higher than acetic acid.

8. The process of claim 1, further comprising separating the crude ethanol product in one or more distillation columns into an ethanol stream and at least one recycle stream.

9. The process of claim 8, wherein at least a portion of the at least one recycle stream is introduced into the vaporizer.

10. The process of claim 9, wherein the at least one recycle stream comprises acetic acid and less than 1 wt. % compounds having a boiling point higher than acetic acid.

11. The process of claim 1, wherein the vapor feed stream comprises at least 70 wt. % acetic acid, based on the total weight of the vapor feed stream.

12. The process of claim 1, wherein the catalyst comprises a combination of metals selected from the group consisting of platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron.

13. The process of claim 1, wherein the vaporizer is constructed of stainless steel.

14. A process for producing ethanol, comprising the steps of:
   introducing acetic acid in a vaporizer to form a vapor feed stream;
   introducing the vapor feed stream into a reactor;
   hydrogenating acetic acid from the vapor feed stream in the presence of a catalyst to form a crude ethanol product comprising ethanol; and
   separating ethanol and at least one recycle stream from the crude ethanol product, wherein the at least one recycle stream comprises acetic acid and less than 1.0 wt. % compounds having a boiling point higher than acetic acid, and wherein the at least one recycle stream is introduced to the vaporizer along with acetic acid to form the vapor feed stream.

15. The process of claim 14, wherein the reactor is operated at an operating pressure from 10 KPa to 3000 KPa, and the acetic acid is vaporized at a temperature below the acetic acid's boiling point at the operating pressure.

16. The process of claim 14, wherein the temperature of the vapor feed stream is less than 160° C.

17. The process of claim 14, further comprising removing a blowdown stream from the vaporizer, wherein the blowdown stream comprises at least 85 wt. % acetic acid and less than 1 wt. % of compounds having a boiling point higher than acetic acid.

18. The process of claim 17, wherein a weight ratio of the vapor feed stream to the blowdown stream is at least 2:1.

19. The process of claim 14, wherein the vapor feed stream comprises at least 70 wt. % acetic acid, based on the total weight of the vapor feed stream.

20. The process of claim 14, wherein the vaporizer is constructed of stainless steel.

21. A process for producing ethanol, comprising the steps of:
   vaporizing acetic acid in a vaporizer in the presence of hydrogen to form a vapor feed stream comprising vaporized acetic acid;
   introducing the vapor feed stream into a reactor; and
   hydrogenating the vaporized acetic acid at an operating pressure of the reactor and in the presence of a catalyst to form a crude ethanol product comprising ethanol, wherein the acetic acid is vaporized at a temperature below acetic acid's boiling point at the operating pressure of the reactor.

22. The process of claim 21, wherein the operating pressure of the reactor is from 10 KPa to 3000 KPa.

23. The process of claim 21, wherein the temperature of the vapor feed stream is less than 160° C.

24. The process of claim 21, further comprising removing a blowdown stream from the vaporizer, wherein the blowdown stream comprises at least 85 wt. % acetic acid and less than 1 wt. % of compounds having a boiling point higher than acetic acid.

25. The process of claim 24, wherein a weight ratio of the vapor feed stream to the blowdown stream is at least 2:1.

26. The process of claim 21, wherein the vaporizer is constructed of stainless steel.

* * * * *